United States Patent
Wang et al.

(10) Patent No.: US 7,312,366 B2
(45) Date of Patent: Dec. 25, 2007

(54) PREPARATION OF ONE INTERMEDIATE FOR PYRETHROIDS

(75) Inventors: Dongchao Wang, Yangzhou (CN); Youfa Jiang, Yangzhou (CN)

(73) Assignee: Jiangsu Yangong Chemical Co., Ltd., Yangzhou, Jiangsu (CN)

( * ) Notice: Subject to any disclaimer, the term of this patent is extended or adjusted under 35 U.S.C. 154(b) by 82 days.

(21) Appl. No.: 10/575,420

(22) PCT Filed: Jan. 13, 2004

(86) PCT No.: PCT/CN2004/000040

§ 371 (c)(1),
(2), (4) Date: Apr. 10, 2006

(87) PCT Pub. No.: WO2005/035474

PCT Pub. Date: Apr. 21, 2005

(65) Prior Publication Data

US 2007/0055075 A1      Mar. 8, 2007

(30) Foreign Application Priority Data

Oct. 10, 2003 (CN) .................. 2003 1 0100116
Dec. 26, 2003 (CN) .................. 2003 1 0122496

(51) Int. Cl.
C07C 33/26 (2006.01)
C07C 69/00 (2006.01)

(52) U.S. Cl. ...................... 568/811; 560/65

(58) Field of Classification Search .................. None
See application file for complete search history.

(56) References Cited

U.S. PATENT DOCUMENTS

| 4,385,070 A | 5/1983 | Bently et al. |
| 4,590,308 A | 5/1986 | Costello et al. |
| 6,759,558 B2 | 7/2004 | Rodefeld |

FOREIGN PATENT DOCUMENTS

| CN | 1380275 | 11/2002 |
| CN | 1458137 | 11/2003 |
| CN | 1204104 | 6/2005 |
| EP | 1247792 | 10/2002 |
| GB | 2127013 | 4/1984 |

OTHER PUBLICATIONS

International Search Report for PCT/CN2004/000040 dated Aug. 26, 2004 (2 pages).

*Primary Examiner*—Sikarl A. Witherspoon
(74) *Attorney, Agent, or Firm*—Osha Liang LLP

(57) ABSTRACT

Methods for preparing 2,3,5,6-tetrafluorodimethylolbenzene, an intermediate for the preparation of pyrethroids, are disclosed. A method for preparing 2,3,5,6-tetrafluorodimethylolbenzene includes the reduction of tetrafluoroterephthalate. Various reduction processes are disclosed, which are simple and safe and can afford the product in high yield and purity. Processes for preparing tefluthrin from 2,3,5,6-tetrafluorodimethylolbenzene, by halogenation, hydrogenation, and esterification, are also disclosed.

23 Claims, No Drawings

PREPARATION OF ONE INTERMEDIATE FOR PYRETHROIDS

TECHNICAL FIELD OF THE INVENTION

The present invention relates to a process for making a polyfluorinated phenyl alcohol, 2,3,5,6-tetrafluorodimethylolbenzene, which is useful as an important intermediate in the synthesis of pyrethroid insecticides and from which tefluthrin may readily be prepared by halogenation, hydrogenation, and esterification.

BACKGROUND OF THE INVENTION

Esters of cis-3-(haloalkenyl)-2,2-dimethylcyclopropanecarboxylic acid with 4-methyl-2,3,5,6-tetrafluorophenyl alcohol, in particular tefluthrin [2,3,5,6-tetrafluoro-4-benzyl-cis-((Z)-2-chloro-3,3,3-trifluoroprop-1-enyl)-2,2-dimethyl-cyclopropane carboxylate], are important insecticidal and acaricidal products. It is thus desired to provide an industrially acceptable and efficient process for making the necessary intermediates such as 2,3,5,6-tetrafluorodimethylolbenzene.

Known processes for preparing 2,3,5,6-tetrafluorodimethylolbenzene are described in some patents. However, further alternative processes that give high quality product in good yield are still required for the production of 2,3,5,6-tetrafluorodimethylolbenzene on an industrial scale.

SUMMARY OF THE INVENTION

The applicant has now found a process for the manufacture of 2,3,5,6-tetrafluorodimethylolbenzene meeting these criteria. In addition, the process is safe and easy to control as compared to existing routes. The process gives the product directly in high yield and with purity up to 97% using simple solvents without the need for additional processing steps, and decreases by-products and waste treatment costs.

There is therefore provided a process for the production of 2,3,5,6-tetrafluorodimethylolbenzene, comprising reducing a tetrafluorodialkylterephthalate in the presence of a reductant and a solvent.

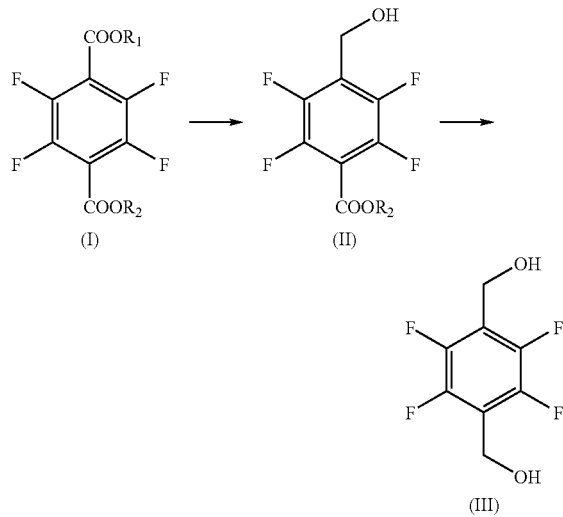

In the context of the present specification, $R_1$ and $R_2$ each independently represents straight or branched alkyl having 1 to 6 carbon atoms, preferably represents methyl, ethyl, n-propyl, n-butyl, n-pentyl, n-hexyl, iso-propyl, iso-butyl, tert-butyl or neo-pentyl, and more preferably, $R_1$ and $R_2$ are identical to each other. Even more preferably, $R_1$ and $R_2$ are both methyl, i.e., the raw material is tetrafluorodimethylterephthalate.

The intermediate (II) may be isolated and purified for further use or the reaction may be allowed to go to completion with the formation of the desired product (III) without the isolation of (II). Compounds of formula (II) are novel and as such form a further aspect of the invention.

DETAILED DESCRIPTION OF THE INVENTION

The starting material (I) may readily be prepared by esterification of the tetrafluoroterephthalic acid with an alkyl alcohol, preferably a lower alkyl alcohol. Tetrafluoroterephthalic acid is an intermediate used in the preparation of insecticides, and can be readily prepared in high yield by hydrolysis of the tetrafluoroterephthalonitrile. Tetrafluoroterephthalonitrile can be readily prepared from tetrachloroterephthalonitrile, which is a commercially available product, through fluorination.

Reductants for the process are suitably selected from metal hydrides, such as lithium, sodium, potassium or calcium borohydrides, such as potassium borohydride and sodium borohydride; metal aluminium hydrides such as sodium aluminium hydride or lithium aluminium hydride; or alkoxyaluminium hydrides such as $MAlH_x(OR)_y$, where M is an alkali metal, R is an alkyl group, and x and y are independently 1, 2 or 3 and x+y=4; aluminium hydride or boride; hydrogen gas; hydrogen donors such as isopropanol, ammonium formate, trialkylammonium formate or cyclohexene.

In the case of reduction with metal hydrides, the amount of metal hydride used in the reduction will depend on the nature of the reductant except for borohydrides, and the molar ratio of the metal hydride to the diester will generally be 1-3:1, preferably 1-1.5:1. For the alkoxyaluminium hydrides, the molar ratio to the diester will generally be 4-12:1, and preferably 4-8:1. If the compound of formula (II) is required, then the amounts of the reductant can generally be decreased by 50%.

Suitable solvents for the reduction include: alcohols; glycols; ethers; glycol ethers; glymes; polyglymes; mixture of lower alkanols (such as, methanol and ethanol); two-phase solvent mixtures; polar inert solvents; organic acids; esters; water; ethers; lower anion surfactants or mixture thereof.

Suitable solvents for the reduction with borohydrides include: alcohols, such as methanol, ethanol, isopropanol; glycols, such as ethylene glycol or polyethylene glycol; ethers such as methyl ether, dioxane, tetrahydrofuran; glycol ethers such as 1,2-dimethoxyethane; glymes such as diglyme; polyethers; mixtures of lower alkanols such as methanol and ethanol. A catalyst or accelerant may be added to increase the yield or rate of the reaction or to decrease the amount of borohydride required to complete the reaction. Suitable accelerants are denaturated metal salts or boron compounds such as boron trifluoride or alkylboron compound. Particularly suitable denaturated metal salts are salts of aluminium, zinc and titanium such as aluminium chloride, zinc chloride, titanium tetrachloride or the like. When sodium or potassium borohydride are used, then a lithium salt such as lithium chloride or bromide can be used as accelerant. The accelerant can be present at 0.05-1 mol, preferably 0.1-0.5 mol per mol of the reductant. Suitable catalysts are onium salts, such as tetraalkylammonium or phosphonium salts, or acyclic or cyclic polyethers. Suitable levels of the catalysts are from 0.01 to 0.1 mol per mol of the reductant.

Alternatively borohydrides may be used in a two-phase mixture of solvents comprising water and a water-miscible or water immiscible solvent such as an aromatic hydrocarbon, especially toluene. In these cases, a catalyst may be added to accelerate the rate of the reaction. Suitable catalysts are onium salts such as tetraalkylammonium salts, phosponium salts, or acyclic or cyclic polyethers such as end-capped polyethylene glycol ethers or crown ethers.

Suitable solvents for aluminium hydride as a reductant are polar aprotic solvents such as aromatic hydrocarbons, for example toluene, anisole, or ethers, for example dioxane, tetrahydrofuran, 1,2-dimethoxyethane, or related oligomeric ethers.

The reduction may be carried out at from −20° C. up to the boiling point of the solvent and is preferably carried out in the range of 30-120° C., more preferably in the range of 40-80° C. The reaction time depends upon the reactivity of the reductant but is generally in the range of 1-20 hrs. In the case of preparation of compound shown by formula (III), the reaction is preferably continued so as to ensure the level of the reaction intermediate (II) is less than 5% and preferably less than 1% of the reaction product.

Alternatively the diester may be reduced into 2,3,5,6-tetrafluoroterephthaldiol using hydrogen gas or a hydrogen donor, such as isopropanol, ammonium formate, trialkylammonium formate or cyclohexene, in the presence of a metal, a metal oxide, a mixed metal oxides, a metal salt or a metal complex catalyst. Examples of the metals are Group VIII metals such as palladium, platinum, rhodium, rhenium or nickel, optionally supported on an inert carrier such as carbon, alumina or an alkaline earth metal carbonate. Examples of metal oxides include copper oxide or chromium oxide or mixed oxides salts such as copper chromite. The amount of the catalyst used depends on the nature of the catalyst. Thus for Group VIII metals, salts or complexes, the amount thereof may be 0.01-5 mol, preferably 0.01-1 mol per mole reductant. For metal oxide or mixed metal oxide catalysts other than Group VIII metals, the amount of the catalyst may be 0.1-10 wt %, preferably 0.1-1 wt % based on the reactant. After the reaction, the catalyst can be recovered from the reaction mass by conventional techniques such as filtration, absorption onto an inert material or precipitation etc to allow it to be recovered for re-use. In the case of hydrogen, the reaction may be carried out under a pressure between 1 and 200 atm, preferably between 10 and 50 atm. The reaction may be conducted at between 50° C. and 200° C., preferably in the range 50-120° C. In the case of a hydrogen donor, the reaction may be carried out at the autogenic pressure of the solvent at the required reaction temperature.

Suitable solvents for the catalytic hydrogenation reduction reaction include alcohols, for example methanol or isopropanol; aromatic hydrocarbons, for example toluene or xylene; ethers, for example tetrahydrofuran or 1,2-dimethoxyethane; organic acids, for example acetic acid; esters thereof such as ethyl acetate, methyl acetate etc. Preferred solvents are isopropanol or mixtures of isopropanol with aromatic solvents. If the compound of formula (II) is desired, then the reaction is stopped after 50% hydrogen has been consumed.

After the reduction reaction, the process may involve one or more of the following steps:
1. filtration to remove catalysts which may then be recovered;
2. quench with water, or an aqueous solution of an organic acid or an inorganic acid;
3. distillation of the reaction solvent for recycle;
4. addition of a different solvent;
5. extraction with water-soluble acid or base to remove water-soluble inorganic residues or un-recovered reaction solvent;
6. recovery of the product by conventional techniques such as crystallization or evaporation of the solvent.

The product may be retained in the solvent and carried forward into subsequent chemical transformation, thus affording a shortened process.

2,3,5,6-tetrafluoroterephthadiol may be converted to tefluthrin by the following steps:
1) halogenation of 2,3,5,6-tetrafluoroterephthadiol to give a 2,3,5,6-tetrafluoro-4-(halomethyl)benzyl alcohol The halogenation of step 1) where the halo group is, for example, chloro or bromo is suitably carried out using hydrohalogen acid, such as aqueous hydrochloric acid or hydrobromic acid. Suitable solvents are inert and water immiscible solvents, such as aromatic hydrocarbons. Preferably, the reaction is performed at a temperature between 50-150° C., preferably at 75-100° C.

2) hydrogenation of the 2,3,5,6-tetrafluoro-4-(halomethyl)benzyl alcohol to give 4-methyl-2,3,5,6-tetrafluorobenzyl alcohol;

The hydrogenation process of step 2) may be carried out by employing hydrogen and a metal catalyst, such as palladium or nickel, in the presence of a base to absorb the liberated hydrogen halide. Suitable bases include alkali or alkaline earth metal hydroxides or carbonates. Suitable solvents include alcohols, esters or aromatic hydrocarbons. The reaction may be carried out at from 0° C. to 60° C. and at from ambient pressure to 10 atm.

3) reaction of 4-methyl-2,3,5,6-tetrafluorobenzyl alcohol with cis-((Z)-2-chloro-3,3,3-trifluoro-prop-1-enyl)-2,2-dimethylcyclopropane carbonyl chloride or cis-((Z)-2-chloro-3,3,3-trifluoro-prop-1-enyl)-2,2-dimethylcyclopropane carboxylic acid to give tefluthrin Tefluthrin can be obtained by esterification. The process of step 3) may be carried out using physical methods for the removal of the formed HCl, such as heating or blowing with an inert gas, or chemical methods such as neutralization by using a base, for example pyridine. The esterification using the cyclopropanecarboxylic acid may be carried out with or without an inert solvent, such as toluene, xylene or the like, in the presence of a strong acid catalyst and with removal of water to drive the reaction to completion.

EXAMPLES

The following examples illustrate various aspects of the invention. However, it should be understood that the present invention should not be limited to these examples in any way.

Example 1

Preparation of 2,3,5,6-tetrafluorodimethylolbenzene (Method 1)

Methanol (500 ml) and sodium borohydride (37 g were added into a four-neck flask (2000 ml). The mixture was heated to 50° C. and the temperature maintained for 1 hour. Tetrafluorodiethylterephthalate (294 g was added into the reactor. The mixture was stirred for 5 hours at 50° C. and then cooled to the ambient temperature. For hydrolysis, 30% hydrochloric acid (300 ml) was added into the mixture, which was then extracted with carbontetrachloride (500 ml). The solution of oil was evaporated under reduced pressure to remove carbontetrachloride, and the titled product, 2,3,5,6-tetrafluorodimethylolbenzene (167.2 g, was obtained as white solid. Purity of the product was 97.7% and the yield was 77.8%.

Example 2

Preparation of 2,3,5,6-tetrafluorodimethylolbenzene (Method 2)

Ethanol (500 ml) and potassium borohydride (54 g were added into a four-neck flask (2000 ml). The mixture was heated to 50° C. and kept at the same temperature for 1 hour. Tetrafluorodimethylterephthalate (266 g was added into the reactor. The reaction was continued at the same temperature for 5 hours and then cooled to the ambient temperature. For hydrolysis, 30% hydrochloric acid (300 ml) was added into the mixture, which was then extracted with carbontetrachloride (500 ml). The solution of oil was evaporated under reduced pressure to remove carbontetrachloride, and the product 2,3,5,6-tetrafluorodimethylolbenzene (176.4 g was obtained. Purity of the product was 98.1% and the yield was 82.4%.

Example 3

Preparation of 2,3,5,6-tetrafluorodimethylolbenzene (Method 3)

The processes in Example 3 are carried out in the same way as in Example 1, except that the amount of methanol was changed to 370 ml. Purity of the product 2,3,5,6-tetrafluorodimethylolbenzene was 93.1% and the yield was 76%.

Example 4

Preparation of 2,3,5,6-tetrafluorodimethylolbenzene (Method 4)

Methanol (500 ml), tetrafluorodipropylterephthalate (161 g and activated palladium (Pd/C, 1.61 g were added to an autoclave (1000 ml). Hydrogen was then passed into the mixture at 60-70° C. under 3.5 atm for hydrogenation. After hydrogen consumption ceased to be obvious, the mixture was cooled and filtered. Pd/C was separated via suction filtration and the filtrate was evaporated under reduced pressure. The white product 2,3,5,6-tetrafluorodimethylolbenzene (85.6 g was collected. Purity of the product was 97.5% and the yield was 79.5%.

Example 5

Preparation of 2,3,5,6-tetrafluorodimethylolbenzene (Method 5)

The processes in Example 5 are carried out in the same way as in Example 4, except that the catalyst is 1.61 g of Raney nickel. Purity of the product was 97.8% and the yield was 80.7%.

Example 6

Preparation of 4-(hydroxymethyl)-2,3,5,6-tetrafluorobenzoate

THF (20 ml), 1,2-dimethoxyethane (10 ml) and sodium borohydride (54 g were added into a dry/clean 100 ml flask. Tetrafluorodimethylterephthalate (4.0 g was slowly added to the reactor, while controlling the temperature at 35° C. Then, the temperature was raised to 70° C. The mixture was stirred under these conditions for 5 hours, while samples were periodically removed for GC (gas chromatography) analysis. The reaction mass was allowed to cool without stirring for 48 hours, then stirred and heated back to 70° C. Analysis showed the reaction was incomplete. Therefore, a further aliquot of 1,2-dimethoxyethane (10 ml) was added, and the reaction stirred under these conditions for a further 5 hrs. GC analysis revealed that the diester had disappeared, and the mixture of compounds of formula (II) and (III) was treated by the addition of water (100 ml), followed by 3×50 ml extractions with ethyl acetate. The combined extracts were treated to provide a sticky white solid. GC analysis revealed that the mixture was comprised of 63% diol and 37% monoester. The product was purified by column chromatography to give 4-(hydroxymethyl)-2,3,5,6-tetrafluorobenzoate. Analytical data: Melting point, 65.6° C., and purity, 97.6%. NMR data: $^{19}F$ ($CD_3OD$) δ −135.2 (multiplet, 2F); −146.3 (multiplet, 2F); $^{1}H$ ($CD_3OD$) δ 4.67 (singlet, —$CH_2$—2H, 3.90 (singlet, $OCH_3$, 3H). Mass Spectrum: Molecule ions peak at m/z 238 (30%) and fragment ion peaks at 207 (100%), 187 (30%), 177 (25%), 159 (20%), 149 (22%), 131 (24 81 (20%), 59 (17%).

Example 7

Preparation (1) of Tefluthrin, [2,3,5,6-tetrafluoro-4-benzyl cis-3-((Z)-2-chloro-3,3,3-trifluoroprop-1-enyl)-2,2-dimethylcyclopropane carboxylate]

Step i. Preparation of 2,3,5,6-tetrafluoro-4-(bromomethyl) benzyl alcohol

A solution (80 g of 2,3,5,6-tetrafluoroterephthadiol in MIBK (methyl isobutyl ketone) was charged to a 1 litre reaction flask equipped with reflux and receive means. The solvent was removed by distillation. Toluene (303 g was added and residual water was removed by azeotropic distillation. The solution was stirred and heated to 60° C. for 30 minutes and Silcolapse (0.2 g and 48% aqueous hydrobromic acid (109.3 g were added to the reaction mixture and this mixture was then heated to 95° C. The distillation apparatus was set to reflux for the initial 30 minutes of reaction at 95° C. Then, azeotropic distillation was carried out for 5.5 hrs to remove water. The mixture was cooled to 55° C. with water (150 ml) and the aqueous hydrobromic acid (36.6 g being added. This mixture was stirred at 55° C. for 15 minutes and then allowed to settle for 30 minutes. The aqueous phase that separated out was removed. The remaining toluene/product layer was further washed with a pre-prepared mixture of water (150 ml) and 40% aqueous sodium acetate solution (36 g. The toluene layer afforded 2,3,5,6-tetrafluoro-4-(bromomethyl)benzyl alcohol product with a yield of 96.2%.

Step ii. Preparation of 4-methyl-2,3,5,6-tetrafluorobenzyl alcohol

The following procedures were carried out in a 1 litre glass autoclave (working volume 350-500 mls) fitted with a dispersion agitator (1000 rpm). $H_2$ gas was fed through a dip-pipe via a Buchi gas controller (Type 6002). The increase/decrease of the temperature is controlled by a Jelabo FP40 external heating/cooling bath. Methanol (362 g, water (6 g, 2,3,5,6-tetrafluoro-4-(bromomethyl)benzyl alcohol (95.1 g 100% wt.), MgO (18.1 g and 5% palladium/carbon catalyst (0.8 g, 100 wt %; Type 58, provided by Johnson Matthey) were charged to the autoclave. The lid was sealed and the autoclave was initially purged with nitrogen to remove residual oxygen (nearly 0), then pressurized to 2.5 bar with hydrogen, and stirred. The pressure was maintained at 2.5 bar by the Buchi controller. The reaction temperature was controlled at 50° C. throughout the reaction by means of the external heating/cooling bath. The reaction was continued until the consumption of hydrogen ceased (typically 60 to 90 minutes). The residual pressure was released and the autoclave purged with nitrogen. The contents of the autoclave were discharged, followed by a small methanol (30 g wash. The spent catalyst and inorganic salts were removed and recovered by filtration. The filter cake was washed with a small amount of methanol (2×30 g. The filtrates and filter-cake washes were combined. On analysis, the reaction had produced 60.4 g of 2,3,5,6-tetrafluoro-4-methylbenzyl alcohol with a yield of 89.4%.

Step iii. Preparation of Tefluthrin

Cis-((Z)-2-chloro-3,3,3-trifluoro-prop-1-enyl)-2,2-dimethylcyclopropane acyl chloride (257 g was charged to a four-neck reactor fitted with an dispersion agitator. Toluene (257 g, molten 2,3,5,6-tetrafluoro-4-methylbenzyl alcohol (188.1 g and suitably added pyridine (51 g were charged together into the dropping funnel. The alcohol solution was dropped to the acyl chloride. The temperature was kept at 35-45° C. during the addition. On completion of the addition, the temperature of the reaction mass was raised to 95° C. and held for 2 hours. The mixture was cooled to 60° C. and washed with water to dissolve the salts and then distilled. The reaction yielded 410.3 g of tefluthrin. Analysis showed that the amount of tefluthrin was 95.5 wt % and the reaction yield was 96.5%.

Example 8

Preparation (2) of Tefluthrin [2,3,5,6-tetrafluoro-4-benzyl cis-((Z)-2-chloro-3,3,3-trifluoroprop-1-enyl)-2,2-dimethylcyclopropane carboxylate]

Methanol (250 ml) and sodium borohydride (20 g were added into a 1000 ml enamel autoclave. Tetrafluorodimethylterephthalate (133 g was slowly added to the reactor while controlling the temperature at 50° C. The mixture was stirred under these conditions for 5 hours and sampled for GC periodically. After GC revealed that the diester had disappeared, 30% aqueous hydrochloric acid (20 ml) was added into the mixture and the resulting mixture was then extracted with tetrachloromethane (250 ml). The tetrachloromethane was removed under reduced pressure and then 48% aqueous hydrobromic acid (122.3 g and toluene (300 ml) were added to the reaction mixture and then the mixture was heated to 95° C. The mixture was refluxed at 95-100° C. for 30 minutes and the toluene water azeotrope was collected. After the reaction was continued for 5.5 hours, the mixture was cooled to 55° C., washed once with 5% aqueous sodium acetate solution and from which toluene as the solvent was removed. Methanol (450 g, water (7.5 g, and 5% palladium/carbon catalyst (1.2 g 100% wt.) were charged to the residue. The lid was sealed and the autoclave was initially purged with nitrogen to remove residual oxygen (to nearly zero) and then pressurized to 2.5 bar with hydrogen. The reaction temperature was controlled at about 50° C. The reaction was continued until the consumption of hydrogen ceased. The residual pressure was released and the autoclave purged with nitrogen. The spent catalyst and inorganic salts were removed by filtration. The solvent was distilled from the filtrate. And then toluene (150 ml) and pyridine (28.8 g were added to the residue. Cis-((Z)-2-chloro-3,3,3-trifluoroprop-1-enyl)-2,2-dimethylcyclopropane formyl chloride (85.8 g was dropped slowly into the mixture when the temperature was heated to 35-45° C. After completion of the addition, the temperature of the reaction mass was raised to 75-90° C. and held for 2 hours. The mixture was cooled to 60° C. and washed with water to dissolve the salts and then distilled to remove solvent. The reaction yielded 71.1 g of tefluthrin, and analysis showed that the amount of tefluthrin was 94.9% by weight and the overall reaction yield from tetrafluorodimethylterephthalate was 64.1%.

The inventors have now found a process for the manufacture of 2,3,5,6-tetrafluorodimethylolbenzene, one intermediate for pyrethroids. By employing the intermediate, Tefluthrin may readily be prepared by halogenation, hydrogenation and esterification. The present process has advantageous of simple and safe processing, high yield, good quality, low cost, and high industry applicability. Moreover, the inventors have also found a new intermediate compound.

We claim:

1. A process for preparing 2,3,5,6-tetrafluorodimethylolbenzene,
represented by the following structural formula, as one intermediate for pyrethroids,

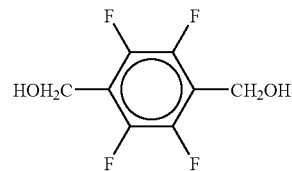

the process comprises a step of reducing dialkyl 2,3,5,6-tetrafluoro terephthalate in the presence of a reductant and a solvent according to the following scheme:

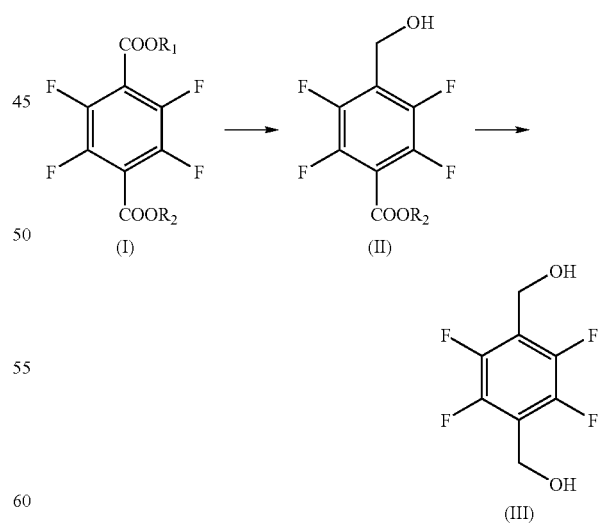

wherein $R_1$ and $R_2$ each independently represents a straight or branched alkyl chain having 1 to 6 carbon atoms.

2. The process according to claim 1, wherein both $R_1$ and $R_2$ are methyl.

3. The process according to claim 1, wherein the solvent is selected from the group consisting of: alcohols; glycols; ethers; glycol ethers; glymes; polyglymes; polyethers; alcohols; two-phase solvent mixtures; polar inert solvents; organic acids; esters; water; anion surfactants or mixture thereof; and mixtures thereof.

4. The process according to claim 3, wherein the solvent is methanol, ethanol, isopropanol, ethylene glycol, polyethylene glycols, diethyl ether, 1,2-dimethoxyethane, dioxane, tetrahydrofuran, diglyme or polyglyme, toluene, xylene, anisole, acetic acid, ethyl acetate, ethyl formate, water, tetrahydrofuran, or a mixture thereof.

5. The process according to claim 3, wherein the solvent is methanol, ethanol, or a mixture thereof.

6. The process according to claim 1, wherein the reductant is a metal hydride, borohydride, a metal aluminium hydride, aluminium borohydride, hydrogen or a hydrogen donor.

7. The process according to claim 6, wherein the borohydride is at least one selected from the group consisting of potassium borohydride, sodium borohydride, and lithium borohydride; and the metal aluminium hydride is lithium aluminium hydride.

8. The process according to claim 1, wherein the reductant is potassium borohydride, sodium borohydride or lithium borohydride and the process is carried out in the presence of a catalyst or an accelerant.

9. The process according to claim 8, wherein the accelerant is a denaturated metal salt or a boride.

10. The process according to claim 9, wherein the denaturated metal salt is one or more selected from the group consisting of aluminium, zinc and titanium salts.

11. The process according to claim 10, wherein the denaturated metal salt is one or more selected from the group consisting of aluminium chloride, zinc chloride, and titanium tetrachloride.

12. The process according to claim 9, wherein the boride is boron trifluoride or alkyl boride.

13. The process according to claim 8, wherein the accelerant is a lithium compound, preferably lithium chloride or lithium bromide, and wherein potassium borohydride or sodium borohydride is used as a reductant.

14. The process according to claim 8, wherein the molar ratio of the accelerant to the reductant is 0.05-1:1.

15. The process according to claim 8, wherein the catalyst is one or more selected from the group consisting of tetra-alkyl ammonium salt, phosphonium salt, and an acyclic or cyclic-polyether.

16. The process according to claim 8, wherein the molar ratio of the catalyst to the reductant is 0.01-0.1:1.

17. The process according to claim 4, wherein the solvent is methanol, ethanol, isopropanol, ethylene glycol, polyethylene glycol, diethyl ether, dioxane, tetrahydrofuran, 1,2-dimethoxyethane, diglyme or polyglyme.

18. The process according to claim 1, wherein the reduction is carried out using hydrogen as the reductant in the presence of at least one catalyst selected from the group consisting of metals, metal oxides, mixed metal oxides, metal salts and metal complex catalysts.

19. The process according to claim 18, wherein the solvent is an alcohol, an aromatic hydrocarbon, an ether, an organic acid or ester thereof.

20. The process according to claim 1 wherein the process is carried out at a temperature from −20° C. to the boiling point of the solvent.

21. The process according to claim 1, further comprising preparing tefluthrin from the 2,3,5,6-tetrafluorodimethylolbenzene with the following steps i) halogenation of the 2,3,5,6-tetrafluorodimethylolbenzene to give a 2,3,5,6-tetrafluoro-4-(halomethyl)benzyl alcohol;

ii) hydrogenation of the 2,3,5,6-tetrafluoro-4-(halomethyl)benzyl alcohol to give 4-methyl -2,3,5,6-tetrafluorobenzyl alcohol;

iii) esterification of the 4-methyl-2,3,5,6-tetrafluorobenzyl alcohol with cis-((Z)-2-chloro-3,3,3-trifluoro-prop-1-enyl)-2,2-dimethylcyclopropane acyl chloride or cis-((Z)-2-chloro-3,3,3 -trifluoro-prop- 1 -enyl)-2,2-dimethylcyclopropanecarboxylic acid to give the tefluthrin.

22. A compound of formula (II),

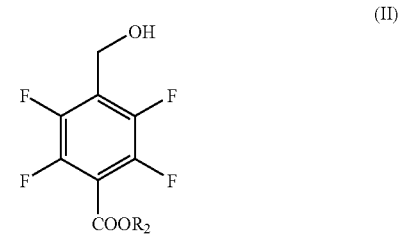

wherein, $R_2$ is a straight or branched alkyl chain having 1 to 6 carbon atoms and is preferably, methyl, ethyl, n-propyl, n-butyl, n-pentyl, n-hexyl, iso-propyl, iso-butyl, tert-butyl or neopentyl.

23. The compound according to claim 22, wherein $R_2$ is methyl.

* * * * *